(12) United States Patent
Richter

(10) Patent No.: US 7,824,613 B2
(45) Date of Patent: Nov. 2, 2010

(54) DELIVERING SAMPLES TO AND CONTROLLING ANALYTICAL INSTRUMENTS

(76) Inventor: Daniel T. Richter, 217 Port St. Claire, Aransas Pass, TX (US) 78336

( * ) Notice: Subject to any disclaimer, the term of this patent is extended or adjusted under 35 U.S.C. 154(b) by 1155 days.

(21) Appl. No.: 11/359,198

(22) Filed: Feb. 21, 2006

(65) Prior Publication Data

US 2007/0196236 A1    Aug. 23, 2007

(51) Int. Cl.
*G01N 21/00* (2006.01)
(52) U.S. Cl. .......................... 422/63; 422/99; 422/100; 422/64; 422/65; 422/66; 198/346.2; 198/347.1; 198/456; 198/463.1; 436/180
(58) Field of Classification Search .......... 422/63–67, 422/99–100; 198/346.2, 347.1, 456, 463.1; 436/180
See application file for complete search history.

(56) References Cited

U.S. PATENT DOCUMENTS

| | | | |
|---|---|---|---|
| 1,733,026 A | 10/1929 | McGuinness | |
| 3,907,231 A * | 9/1975 | Kreiner | ........................ 406/19 |
| 3,945,682 A | 3/1976 | Hoagland | |
| 4,582,990 A * | 4/1986 | Stevens | ...................... 250/328 |
| 4,886,401 A | 12/1989 | Andrews | |
| 4,941,777 A | 7/1990 | Kieronski | |
| 4,960,350 A | 10/1990 | Tsubata | |
| 5,234,292 A | 8/1993 | Lang | |
| 5,370,215 A * | 12/1994 | Markin et al. | ............. 198/346.1 |
| 5,441,699 A | 8/1995 | So et al. | |
| 5,623,415 A | 4/1997 | O'Bryan | |
| 5,805,454 A | 9/1998 | Valerino | |
| 6,128,549 A | 10/2000 | Swartz | |
| 6,141,602 A | 10/2000 | Igarashi | |
| 6,659,693 B1 | 12/2003 | Perkins | |
| 6,942,133 B2 | 9/2005 | Frankeberger | |
| 2002/0198738 A1 | 12/2002 | Osborne | |
| 2004/0100415 A1 | 5/2004 | Veitch | |

* cited by examiner

*Primary Examiner*—Jyoti Nagpaul
(74) *Attorney, Agent, or Firm*—G. Turner Moller

(57) ABSTRACT

A control system for a bank of analytical instruments operates the instruments as a group rather than singly. The system includes an autoloader at a sample preparation station into which an individual loads sample vials of unknown material. A second autoloader provides sample vials of known material that can be used to calibrate instruments. A computer controls the autoloader and a conveyor system to deliver a selected one of the vials to a selected instrument. The conveyor system includes a group of distributors, typically in series, to deliver a vial to any one of a large group of instruments. The conveyor system is preferably a pneumatic system including a receiver and technique for slowing the vials down when they approach the receiver. The receiver is positioned to deliver the vial to an autoinjector of the instrument. A computer monitors and communicates with the analytical instrument to obtain inputs to control components of the system.

21 Claims, 6 Drawing Sheets

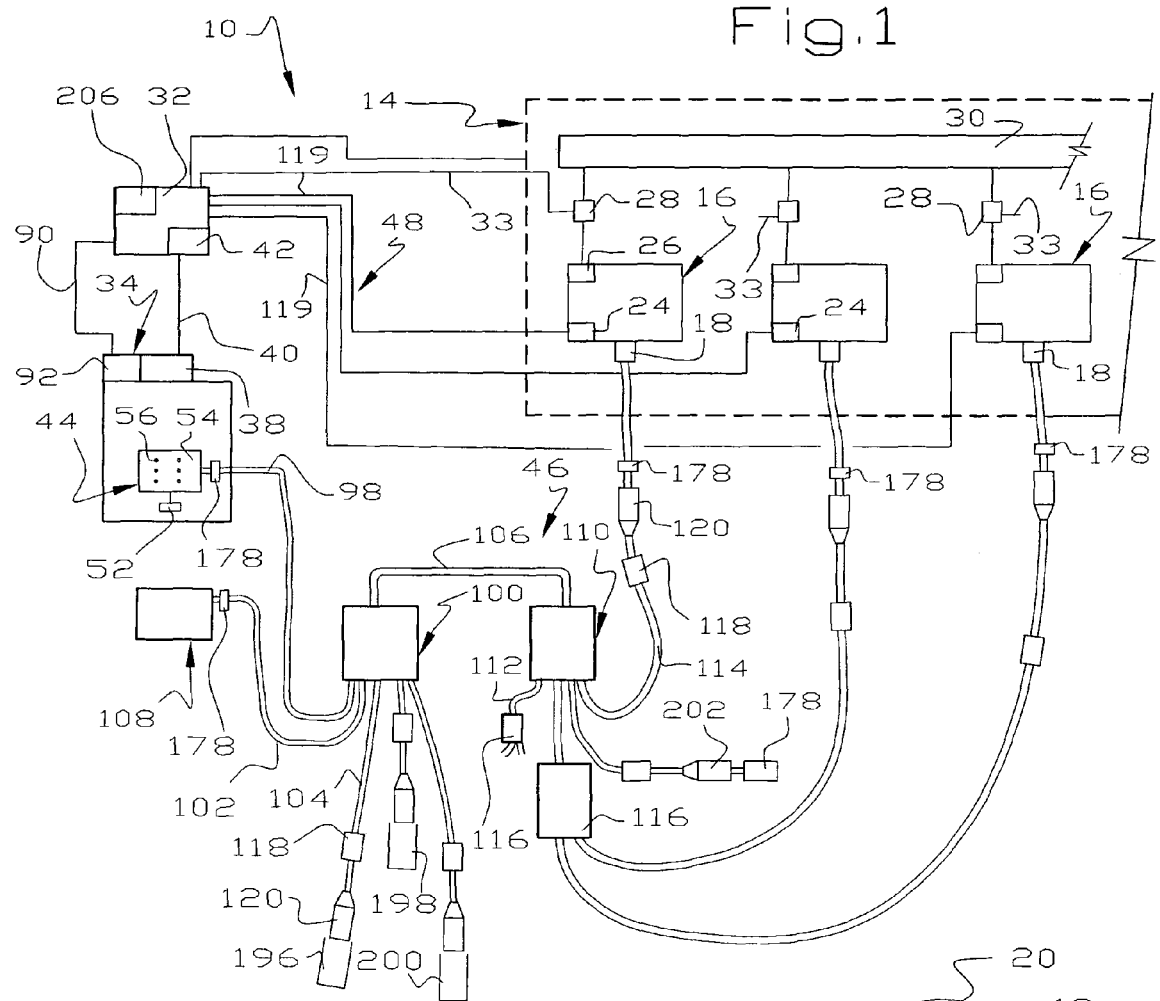

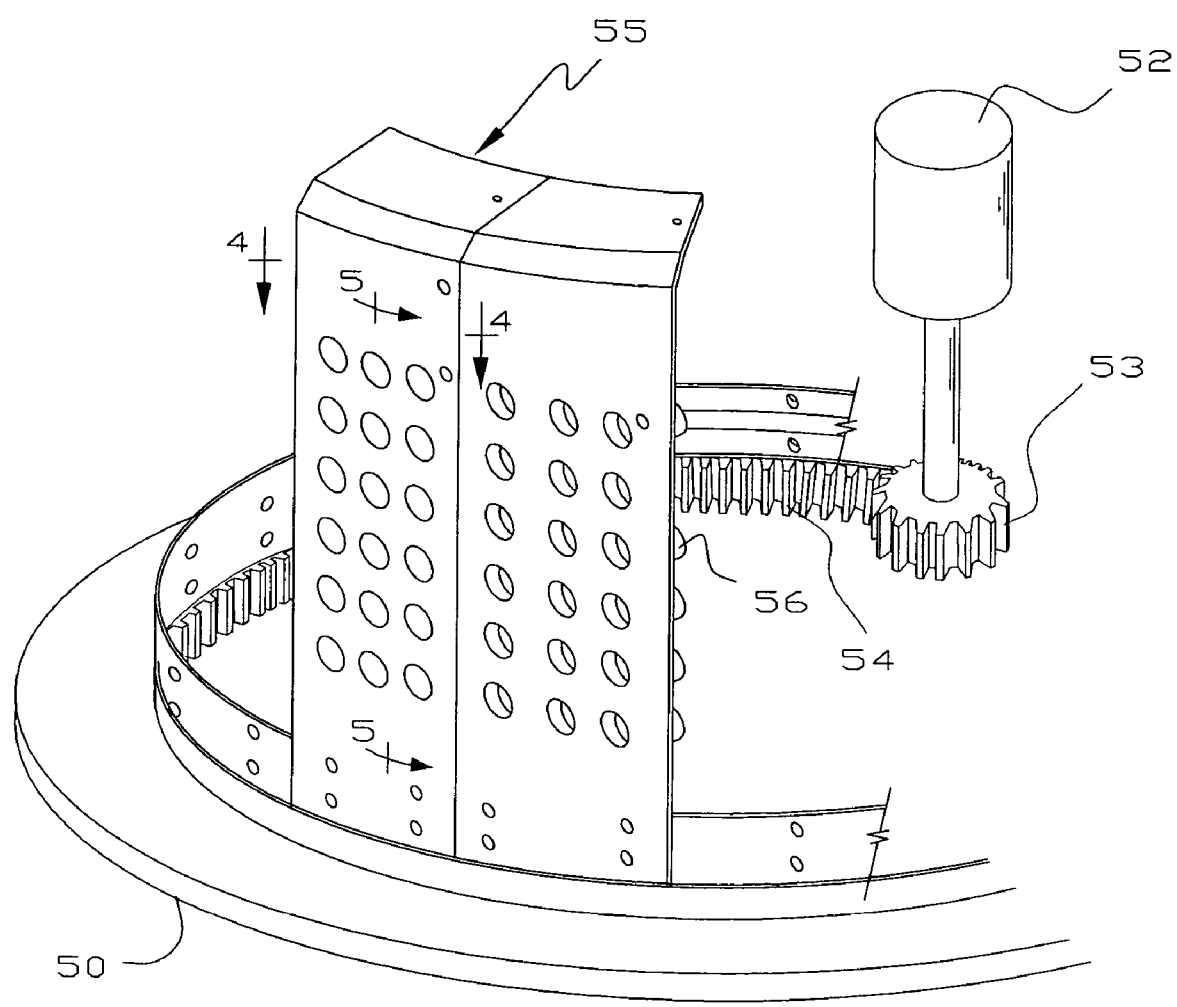

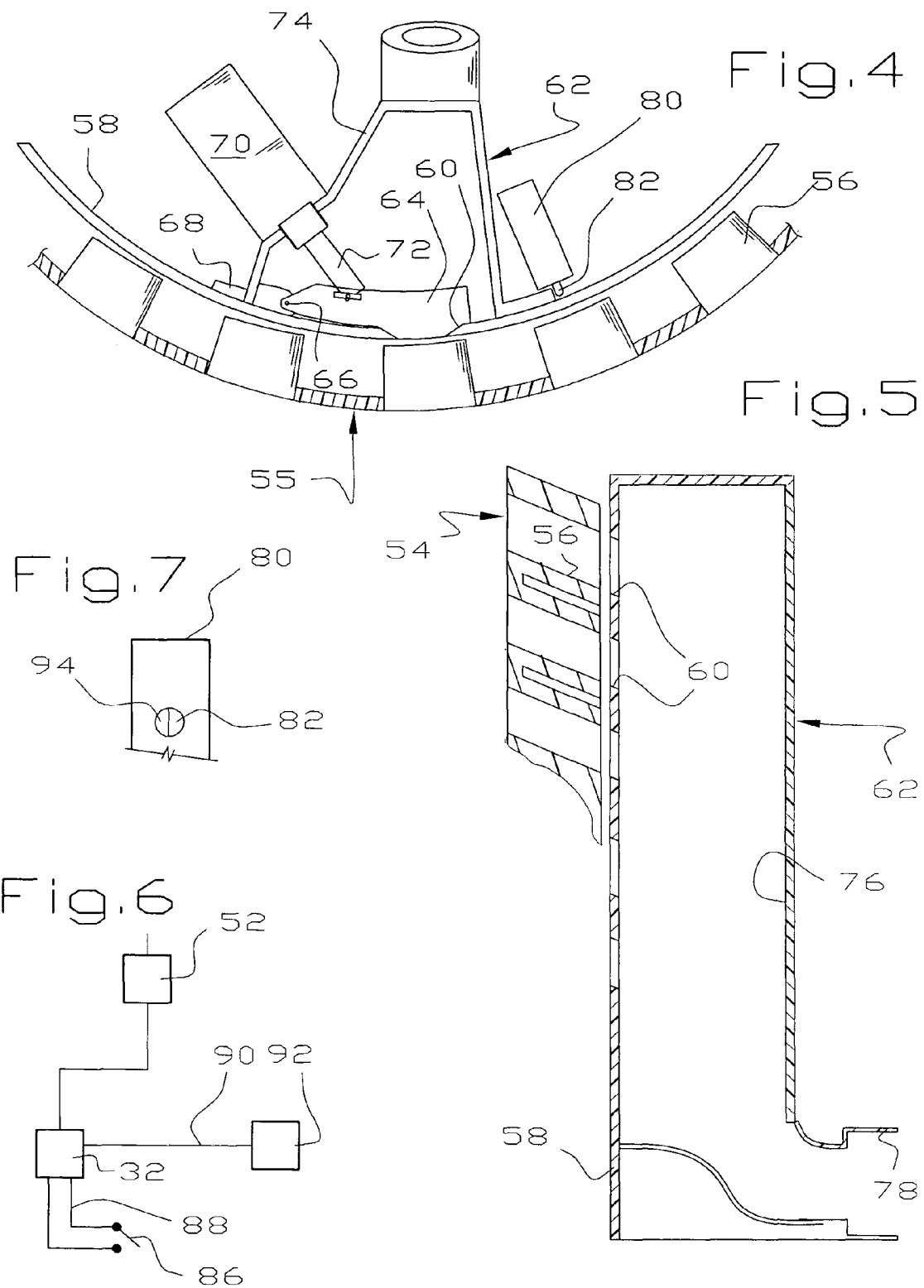

DELIVERING SAMPLES TO AND CONTROLLING ANALYTICAL INSTRUMENTS

This invention relates to a system for delivering samples to and operating a bank of analytical instruments, particularly gas chromatographs, mass spectrometers, viscosimeters, densimeters, blood test equipment, urinalysis equipment and the like.

BACKGROUND OF THE INVENTION

There are many situations where large number of analytical instruments are used to conduct large numbers of chemical, physical or biological tests on liquids. A prime example is an oil refinery where crude oil is distilled, cracked, reformed and the like to produce a variety of liquid hydrocarbon products. Modern refineries have extensive laboratories to run analytical tests on liquids that are intermediate products as well as end products in order to generate information leading to more efficient operation of the refinery. One known refinery has thirty gas chromatographs and a sizeable number of mass spectrometers in an analytical lab. Other examples of laboratories having large numbers of analytical instruments will be apparent to those skilled in the art such as pharmaceutical operations, medical laboratories, food manufacturing operations and the like.

Typically, a sample is taken at a location in the refinery or plant and delivered to a sample preparation station where an individual withdraws a suitably sized portion and places it in a clean specialized container known as a vial. Records are made to indicate when and where the sample was taken and suitable information is placed on the sample container so results can be appropriately correlated for study and analysis.

In a typical large analytical laboratory, such as may be found in chemical plants, oil refineries, medical laboratories, contract laboratories and the like, sample vials are loaded in a tray and manually delivered from the sample preparation station to a bank of analytical instruments, of which gas chromatographs (GCs) or combinations of gas chromatographs and mass spectrometers (MSs) are common. An individual loads the vials into the inlet tray or autoloader of the GCs or MSs and the analytical instruments more-or-less operate automatically to conduct the programmed tests on the samples in the vials, generate reports and transport the vials to an output tray of the instrument where the vials are ultimately collected and either discarded or temporarily stored.

Disclosures of some interest relative to this invention are found in U.S. Pat. Nos. 1,733,026; 4,491,777; 4,886,401; 5,234,292; 5,441,699; 5,623,415; 5,805,454; 6,128,549; 6,141,602 and 6,659,693 and patent publications 2002/0198738 and 2004/0100415.

SUMMARY OF THE INVENTION

In this invention, it is recognized that considerable efficiencies are achieved by a systems approach to large banks of analytical equipment. For example, in a typical oil refinery laboratory having many GCs and MSs, it often happens that one or more GCs will appear to be fully loaded but the programmed tests are of relatively short duration, meaning that a particular GC may run out of samples to test while adjacent GCs have many samples yet to run. Similarly, a GC or MS may malfunction for one reason or other and not be noticed so that samples in its inlet tray are not run while other equipment may be idle thereby reducing the throughput and efficiency of the lab. Preliminary tests of this invention suggest that operating efficiencies of a bank of analytical instruments may be increased on the at least on the order of 20%. This is no small affair because a modern GC may cost $50,000 and MSs are equally or more expensive. In a lab of a large number of instruments, it will be apparent that a sizeable increase in efficiency is of considerable value. In addition, there is always a concern about a particular aspect of reliability, i.e. whether the test results are correctly correlated to the appropriate sample. An increase in reliability, while more difficult to measure, is always sought after and welcome if achieved. This is of particular concern in medical laboratories where correct results attributed to the wrong patient is a recipe for disaster.

In this invention, a conveyor or transport system is provided from a sample preparation station to each of a plurality of analytical instruments. A prepared sample container or vial is placed in an inlet or autoloader. The system monitors the operation of all of the analytical instruments and delivers the vial to an appropriate one of the instruments, taking into account the nature of the test to be run, the capability of all of the instruments in the bank, the operability of all of the instruments in the bank of instruments and other criteria affecting efficiency of the bank.

The conveyor system is preferably a pneumatic system in which differential air pressure, either positive or negative, moves the vials from the inlet through a distributor to the inlet of an appropriate one of the analytical instruments, e.g. the autoloader or injector of a GC. Typically, the vial inventory of the system is held in an autoloader located at the preparation station in contrast to the prior art where the vial inventory is held in the inlet tray or autoloader of the individual instrument. In the event one of the instruments malfunctions, a signal is generated by the instrument and acted upon by the system of this invention so an attendant can investigate the cause and provide a solution. At the same time, sample vials are directed elsewhere until the problem is resolved. After the tests on a particular vial are complete, the vial is delivered to an outlet tray of the instrument and a conveyor system of this invention retrieves the vial and delivers it to a disposal or storage station. The operation of the system is conducted by a controller or computer connected to the analytical instruments and to various components of the system.

Another important feature of this invention is the ability to more-or-less automatically retrieve and run calibration samples from one or more storage stations having samples of known composition and concentration.

It is an object of this invention to provide a system for transporting sample containers to and/or from a bank of analytical instruments.

A further object of this invention is to provide an improved system for handling sample containers and improve the efficiency of a bank of analytical instruments.

A more specific object of this invention is to provide improved components in a pneumatic conveyor system for handling sample vials.

These and other objects and advantages of this invention will become more apparent as this description proceeds, reference being made to the accompanying drawings and appended claims.

BRIEF DESCRIPTION OF THE DRAWINGS

FIG. 1 is a schematic view of an analytical laboratory control system of this invention;

FIG. 2 is an isometric view of a sample vial having a marker or recording device thereon containing information about the sample in the vial;

FIG. 3 is a partial isometric view of part of an autoloader provided at a sample preparation station for receiving and accumulating an inventory of sample vials and for launching the vials into the conveyor system;

FIG. 4 is a horizontal cross-sectional view of the autoloader of FIG. 3, taken substantially along line 4-4 thereof as viewed in the direction indicated by the arrows, illustrating a mechanism for retrieving one vial at a time from the autoloader;

FIG. 5 is a vertical cross-sectional view of the autoloader of FIG. 3, taken substantially along line 5-5 thereof as viewed in the direction indicated by the arrows, illustrating a manifold for receiving vials from one of a series of sleeves and delivering them to a common outlet, certain components being eliminated for clarity of illustration;

FIG. 6 is a schematic view of a system to convert the autoloader from a filling mode to an emptying mode;

FIG. 7 is a partial broken view of an end of a circuit board showing a light source and a photocell;

DETAILED DESCRIPTION

Figure 8:
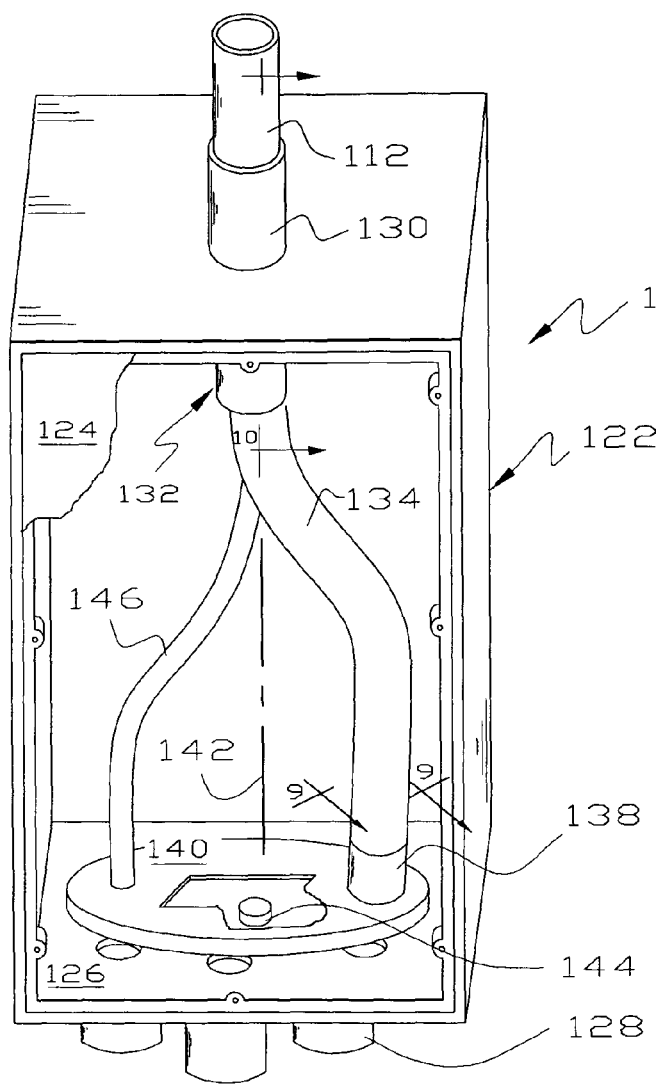
FIG. 8 is a broken isometric view of a vial distributor used in the system of FIG. 1 to receive vials from an autoloader and deliver vials downstream in a path dictated by a controller.
Figure 10:
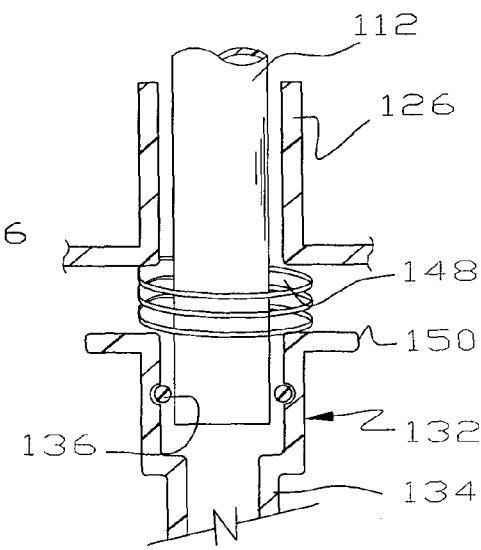
FIG. 10 is an enlarged cross-sectional view of the vial distributor of FIG. 8, taken substantially along line 10-10 thereof as viewed in the direction indicated by the arrows.
Figure 9:
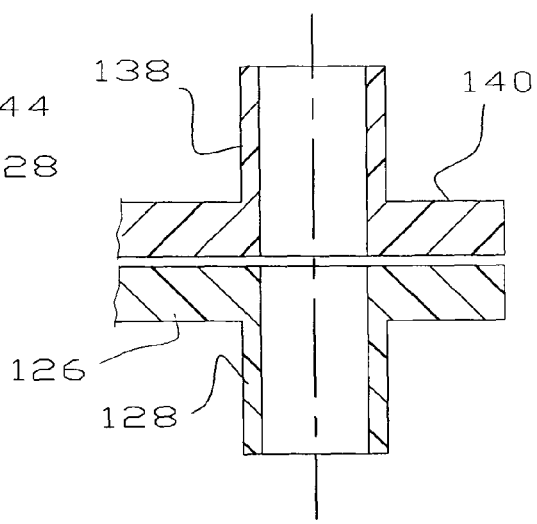
FIG. 9 is an enlarged cross-sectional view of the vial distributor of FIG. 8, taken substantially along line 9-9 thereof as viewed in the direction indicated by the arrows.

Referring to FIGS. 1-11, there is illustrated a system 10 for handling a large number of sample containers or vials 12 in an analytical laboratory 14 having a large number of analytical instruments 16 such as gas chromatographs, mass spectrometers, viscosimeters, densimeters, blood test equipment, urinalysis equipment and the like which have heretofore been operated singly rather than as a bank of interrelated instruments. For purposes of convenience, the system 10 will be described in conjunction with a bank of GCs, it being understood that the system is equally useful with a bank of other analytical instruments or a bank of mixed analytical instruments. It will also be understood that the bank of analytical instruments may include instruments not controlled, or only partially controlled, by the system 10.

A typical analytical laboratory 14 may include a bank of GCs 16 having a conventional autoinjector 18 which receives a conventional vial 12 having a septum 20 in the lid 22 so a sample of the liquid in the vial 12 may be withdrawn by a sampling needle (not shown) in the GC, as is conventional in modern GCs. It will be understood that other modern analytical instruments have similar automatic injectors for processing a sample vial after it reaches the instrument.

Each GC includes a communication port 24, which in current versions of GCs is a serial port, so that external devices may communicate with the GC, and the GC may communicate with external devices, in accordance with protocol dictated by the GC manufacturer. Although the communication links illustrated in FIG. 1 are wires, it is apparent that communication may be by some wireless technique. Each GC includes an output device or detector 26 from which analog data emerges and is converted into digital information by a converter 28 which delivers information to a computer 30 having controlling software therein which receives information from the converters 28, merges the data into useable form, prepares suitable reports and the like. Those skilled in the art will recognize the laboratory 14 to be a typical modern analytical laboratory having a bank of analytical instruments.

In one embodiment of this invention, a computer 32 of the system 10 controls the delivery of vials 12 to the instruments 16 in response to an input from the instruments 16 and does not modify the assembly of data in the computer 30. In another embodiment of this invention, data from the converters 28 is delivered through a communications link 33 to the computer or controller 32 where the data is modified and put into the form of reports. In either event, the computer 32 is capable of monitoring operation of the instruments 16 and using inputs from the instruments 16 to modify operation of the system 10 in a manner more fully apparent hereinafter.

Not too far from the instruments 16 is a sample preparation station 34. The station 34 may be in the same building or room as the analytical instruments 16 or located elsewhere within a reasonable distance. A sample taken at a location in the refinery or plant is delivered to the sample preparation station 34 where an individual withdraws a suitably sized portion and places it in one of the vials 12 and provides suitable information on a device 36 on the vial 12 by use of an encoding device 38 so the results from the tests done by the instruments 16 may be appropriately correlated and analyzed. The nature of the sample depends on the type material involved and the tests being run. Typically, the sample is a liquid. Occasionally, the sample is a solid which is dissolved in a suitable liquid at the preparation station. In any event, each sample is labelled, put in an appropriate container or vial and modified if necessary to be compatible with the instrument 16 which is going to be used to test it.

The device 36 may be of any suitable type. In the past, the device 36 might have been a simple tag having identifying information thereon, a bar code or the like. Current technology, such as RFID's, are also eminently suitable for the device 36. In any event, information such as an identifying number or symbol, the source of the sample in a particular vial 12, its nature and other suitable information is encoded in any suitable manner on a device 36 at the sample preparation station 34 and transmitted through a communication link 40 to a data base 42 comprising part of the software operating the computer 32. As will become more fully apparent hereinafter, the computer 32 also functions as a controller of the system 10 of this invention.

The system 10 accordingly comprises, as major components, the computer 32 which acts as a system controller, the encoding device 38 and communication link 40, an autoloader 44 which receives vials 12 from an operator at the sample preparation station 34, a conveyor system 46 for delivering vials from the autoloader 44 to a selected one of the instruments 16, and a communication system 48 incorporating a series of communication links between the controller 32, the instruments 16 and various components of the conveyor system 46.

As shown best in FIGS. 1 and 3-7, the autoloader 44 includes a rotatable base 50 under the control of a suitable stepper motor 52 driving a spur gear 53 meshing with a set of gear teeth 54. The base 50 provides a series of panels 55 providing a series of vertical rows of vial receiving sleeves 56. Inside the panels 55 is a stationary cylinder 58 having only one series of vertical openings 60 leading to a manifold 62. Closing each of the openings 60 is a trap door 64 connected by a pivot pin 66 to a bracket 68 fixed to the cylinder 58. A solenoid 70 on the bracket 68 provides an output rod 72 connected with the trap door 64 for pulling the trap door 64 open thereby allowing a vial 12 in a particular sleeve 56 to slide downwardly into the manifold 62 in response to a signal from the computer 32. It will accordingly be seen that the only vials 12 that can slide into the manifold 62 are those aligned with the openings 60 while the trap doors 64 normally close each of the openings 60. It will be seen that the autoloader 44 provides the capacity to hold hundreds of vials 12 while delivering a selected one of the vials at a time to the manifold 62 and thus to the conveyor system 46.

The manifold 62 comprises a closed wall 74 providing a chamber 76 adjacent each of the openings 60 to direct a downwardly sliding vial 12 toward an outlet 78. It will accordingly be seen that if a particular trap door 64 is opened, the vial 12 in the sleeve 56 aligned with the opening 60 is able to slide into the manifold 62. A vacuum applied to the manifold 62 will accordingly deliver the vial 12 to the conveyor system 46.

An important feature of the autoloader 44 is that it indicates to the operator at the sample preparation station 34 where a particular vial 12 is to be placed. To this end, the autoloader 44 includes a circuit board 80 having a series of LEDs or other light sources 82 so that there is a single vertical row of sleeves 56 adjacent the manifold 62 which can be illuminated. Because the rotational position of the base 50, and therefore the rotational position of the vial receiving sleeves 56, is controlled by the stepper motor 52 which is under the control of the computer 32, the row of sleeves 56 to be filled is under the control of the computer 32 thereby indicating to the sample preparation worker which row is to be filled with vials. The particular sleeve 56 to be filled is, of course, indicated by illumination of only one of the light sources 82.

Because the autoloader 44 is being filled during the same time interval that vials 12 are being withdrawn, some technique is needed to convert the autoloader 44 back and forth between a filling mode and an emptying or transporting mode. Although any suitable technique is feasible, one such device is shown in FIG. 6 where a foot pedal or other similar selector 86 communicates through one or more communication links 88 to the computer 32 to tell the stepper motor 52 what to do. The normal mode is preferably the emptying or transporting mode. If the pedal 86 is depressed into the filling mode, the computer 32 instructs the motor 84 to position the base 50 so a particular light source 82 illuminates the particular sleeve 56 that the computer 32 wants filled. To change to the emptying or transporting mode, the computer 32 sends a signal through a communication link 90 to a monitor 92 to tell the preparation station worker that one of the GCs is finished with a prior test and needs a new vial 12. At an appropriate time, the worker releases the selector 86 so it moves to the emptying mode whereupon the computer 32 instructs the stepper motor 52 to rotate the base 50 to the appropriate angular position where the next vial is located and energizes the appropriate solenoid 70 to open the appropriate trap door 64 to allow the appropriate vial 12 to enter the conveyor system 46. After the desired vial is retrieved, the computer 32 instructs the stepper motor 52 to return the base 50 to the angular position where vial loading is being conducted.

The row of sleeves 56 in the autoloader that is being loaded is loaded in a predetermined manner, e.g. from top to bottom. Thus, after the preparation station worker inputs the data for a particular vial 12 into the device 36, the computer 32 knows the location of a particular vial so it may be retrieved at an appropriate time. It will accordingly be seen that the autoloader 44 and computer 32 cooperate to provide a technique indicating to the attendant which sleeve 56 a particular vial is to be placed.

It is preferred that the autoloader 44 provide some technique for insuring that a particular vial is placed in the particular sleeve 56 designated by the computer 32. To this end, a technique is provided to indicate that a vial has been placed in the desired sleeve 56. One convenient technique for this purpose is shown in FIG. 7 where a photocell 94 is placed immediately adjacent the light source 82 but shielded from direct light from the source 82. Under some conditions, a separate reflector 96 is provided on the base of the vial 12, as shown in FIG. 2, to reflect light from the source 82 into the photocell 94 thereby indicating to the computer 32 of the presence of the vial 12 in the appropriate sleeve 56, meaning that the appropriate vial 12 has been placed in its designated or known sleeve 56. Given the correct design and/or an appropriate liquid in the vial 12, light reflected off the base of the vial 12 may be sufficient to energize the photocell 94 without requiring a separate reflecting member. If the vial 12 is placed in an incorrect sleeve 56, the computer 32 recognizes that something is amiss and provides a suitable signal or instruction and/or shuts down the operation. Components which incorporate both the LED 84 and the photocell 94 are known in the art as photointerrupters and are commercially available from Sharp Microelectronics or Fairchild.

It will be seen that vials are selected from the autoloader 44 and launched under control of the computer 32 and delivered to the conveyor system 46 which is also controlled by the computer 32 to deliver the desired sample vial 12 to a selected one of the instruments 16. The conveyor system 46 is preferably a pneumatic system, operating under either positive or negative air pressure, to deliver the vials 12 through the outlet 78 of the autoloader and a conduit 98 to a first distributor 100 having two inlet conduits 98, 102 and two additional conduits 104, 106 which may be either inlet or outlet conduits, depending on which direction the vials 12 are being transported.

The inlet conduit 102 leads to a second autoloader 108, which may be identical to the autoloader 44, and which preferably contains a larger number of vials 12 containing known liquids of known concentration. The autoloader 108 accordingly provides a series of calibrated samples which may be run on the instruments 16 at any time, under the control of the computer 32, to calibrate the instruments 16 in accordance with a predetermined schedule or upon the occurrence of an event that suggests calibration is necessary or desirable. It will accordingly be seen that an important feature of this invention is the ability to calibrate the instruments 16 at any time. It will be apparent that the vials of calibrated liquids may be stored in the autoloader 44, although it is preferred to provide a separate autoloader.

In FIG. 1, the conduit 106 leads to a second distributor 110 having a series of conduits 112, 114 which may be either inlet or outlet conduits, depending on the direction the vials 12 are being transported. The number and arrangement of the second distributors 110 depend on the number and type of analytical instruments 16 in the laboratory 14 equipped with the control system 10 of this invention. The distributor 116 shown in FIG. 8 provides an inlet and eight outlets, meaning that if only eight instruments 16 are in the laboratory 14, only one distributor 116 is needed. It will accordingly be seen that the arrangement of the conduits 112, 114 varies from one situation to the next. For purposes of illustration, two of the conduits 112 are shown as connected to additional distributors 116 while the conduit 114 is shown as connected to one of the instruments 16 through a sensor 118 and a receiver 120. It will accordingly be apparent that a very large number of instruments 16 may be controlled by the system 10 of this invention simply by placing as many distributors 116 in series as are necessary.

In any event, it will be seen that each of the instruments 16 is connected to a distributor 116 by a conduit, sensor 118 and receiver 120. As will become more fully apparent hereinafter, the computer 32 is connected by a communication link to each of the distributors 110, 116 to control the ultimate destination of a particular vial 12. Accordingly, a particular vial 12 retrieved from the autoloader 44 may be delivered to a selected one of the instruments 16 with appropriate instructions being delivered by a communication link 119 to the communication port 24 of the instrument 16 to conduct a particular test.

Although the distributors 110, 116 may be of any suitable type, a preferred construction is illustrated in FIG. 8. Although the distributors 110, 116 do not have to be identical, it is desirable that they are. The distributor 116 preferably comprises a container or housing 122 having a removable front 124 and a bottom wall 126 providing a series of sleeves 128 opening into the interior of the container 122 and connected to the suitable conduits 112, 114. An inlet conduit 112 passes though a sleeve 130 on top of the container 122 and connects to a slip joint 132 having the capacity to allow a lower conduit or article director 134 to rotate relatively frictionlessly relative to the conduit 112 without leaking substantial quantities of air. For purposes more fully apparent hereinafter, the slip joint 132 also allows linear, or in and out, movement of the conduit 112 relative to the slip joint 132. If desired, an O-ring 136 may be provided in the slip joint 132 to seal the joint against air loss. In many situations, however, the O-ring 136 may prove to be unnecessary.

The conduit 134 is curved and connects to a sleeve 138 on a rotatable disc 140 which is rotatable about an axis 142 under the control of a stepper motor 144 located on the underside of the bottom wall 126. One or more curved struts 146 connect the disc 140 and the curved conduit 134 to provide structural strength.

It is preferred to provide some means to reduce air loss between the disc 140 and the bottom wall 126. The simplest technique is to provide a spring 148 pushing down on a flange 150 of the slip joint 132. This pushes the flat bottom of the disc 140 against the flat bottom wall 126 thereby minimizing air loss. The slip joint 132, either with or without the O-ring 136, accommodates the relative rotational and linear movement between the inlet conduit 112 and the curved conduit 134.

It will be seen that the sleeves 128 connect to suitable conduits 112, 114 leading to downstream distributors or directly to an instrument 16. The stepper motor 144 is under the control of the computer 32 through a suitable communication link and is accordingly capable of rotating the disc 140 to a position to direct a vial 12 toward the desired instrument 16 or downstream distributor. With a distributor 110 having eight outlet sleeves 128 in series with two distributors 116 having eight outlet sleeves 128 as shown in FIG. 1, it will be seen that a predetermined path is provided to twenty one instruments 16. In the event there are more than twenty one instruments 16 in the laboratory 14, it is a matter of providing additional distributors in series with either the distributor 110 or one of the distributors 116.

The purpose of the sensor 118 is to detect an incoming vial 12, turn off the propelling fluid and allow the vial 12 to coast into the receiver 120. To this end, the sensor 118 may be a conventional photocell providing a light path that is interrupted by the passing vial 12. A communication link to the computer 32 allows the computer 32 to detect when the vial 12 passes the sensor 116 and turn off the propulsion fluid. In a prototype of the control system 10, the sensor 118 is located five feet upstream from the receiver 120.

In the two dimensional view of FIG. 1, it appears that the receiver 120 is located below the autoinjector 18 of the instruments 16. In fact, the last few feet of the conduit 114 and the receiver 120 are located vertically above the autoinjector 18 so the vial 12 is delivered lid side up into the normally upwardly open inlet slot of the conventional autoinjector 18 and the autoinjector 18 works in its conventional manner. In other words, the vials 12 are presented to the autoinjector 18 in the same orientation and manner as the vials 12 are presented by conventional autoloaders (not shown) provided by conventional analytical instruments.

Figure 11:
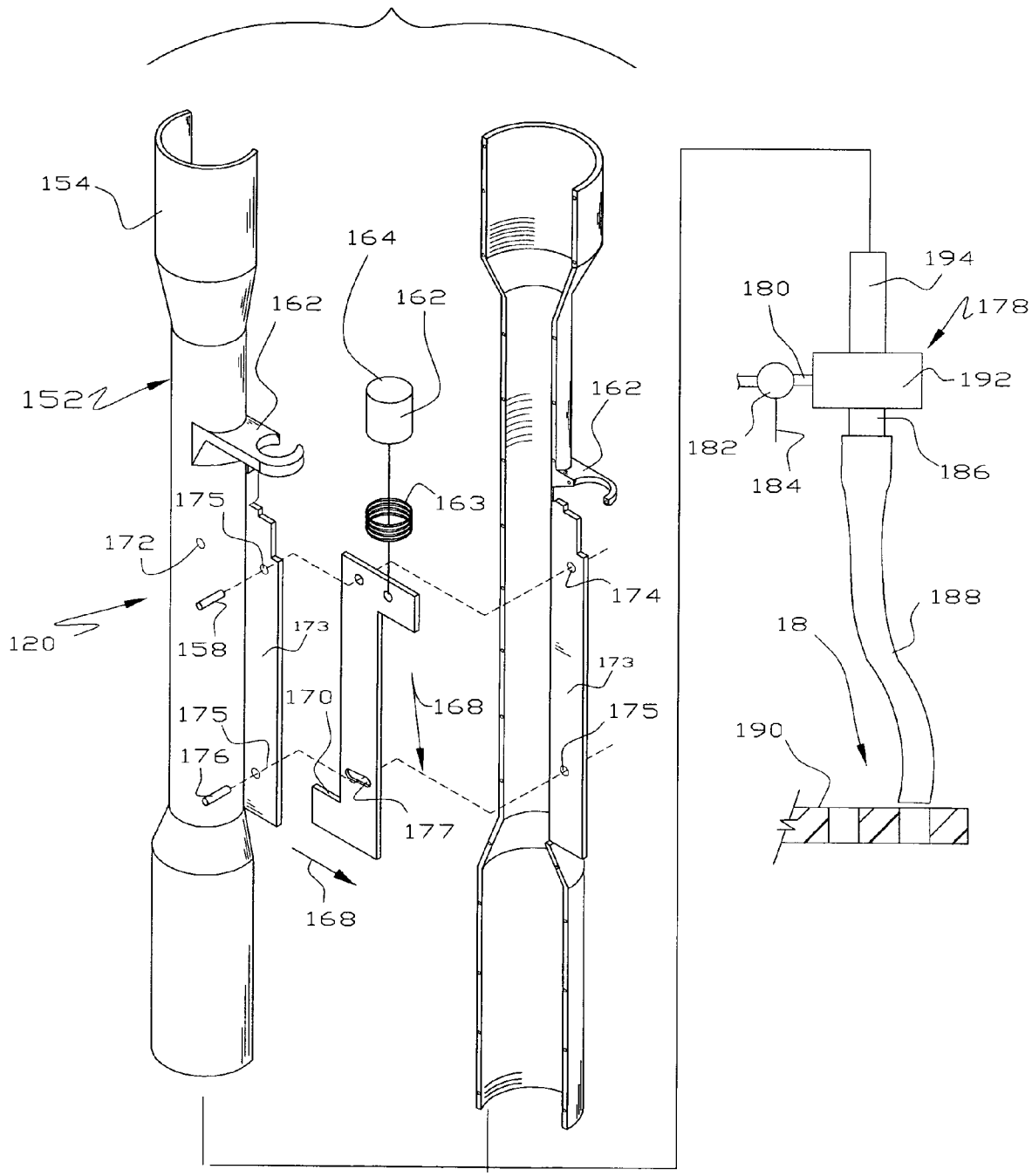
FIG. 11 is an exploded isometric view of a vial receiver used in the system of FIG. 1.

Referring to FIGS. 1 and 11, the receiver 120 is of unusual design and comprises a two part housing 152 having essentially mirror image halves providing an upper end 154 for receiving vials 12 being delivered to the instrument 16, a movable gate 156 pivoted by a pin 158 to the housing 152, and a solenoid 160 or other suitable device mounted on a bracket 162 to open the gate 156 and allow the vial 12 to fall into the autoinjector 18 under the control of the computer 32 through a suitable communication link 164. The gate 156 is biased by the spring 163 so an edge 166 is inclined inside the housing 152 in a normal at rest position.

The upper housing end 154 connects to the conduit 114 so the vial 12 moves into the housing 152 and contacts the edge 166 of the gate 156 and biases the gate 156 outwardly in the direction shown by the arrow 168 thereby slowing the vial 12 preparatory to stopping against a shoulder 170 on the gate 156. The computer 32 knows the vial 12 is approaching its intended receiver 120 because of a signal from the sensor 116. An additional photocell 172 may be provided on the receiver housing 152 to positively detect that the vial 12 has reached its intended receiver. The computer 32 then directs the solenoid 162 to open the gate 156 and thereby drop the vial 12 into the autoinjector 18 of the intended instrument 16. The autoinjector 18 operates in a conventional manner to withdraw a sample from the vial 12 and the instrument 16 functions in its normal and intended manner to analyze the liquid sample in the vial 12.

As shown in FIG. 11, the housing 152 includes a pair of flanges 173 providing aligned openings 174 for receiving the pivot pin 158 and a pair of aligned openings 175 for receiving a pin 176 passing through an arcuate slot 177 in the gate 156. Cooperation between the pin 176 and the slot 177 controls the arc of pivotal movement of the gate 156 within predetermined limits.

The conveyor system 46 includes a source of gas under pressure, such as a source of liquid nitrogen or, preferably, one or more pumps. As shown in FIGS. 1 and 11, a series of pumps 178 used to deliver air through the conveyor system 46. The pumps 178 have the capability of applying negative pressure to the autoloaders 44, 108 to withdraw a vial 12 therefrom or to withdraw a vial 12 from the autoloaders 18 of the instruments 16. In addition, the pumps 178 have the simultaneous capability of delivering positive pressure in the opposite direction to propel the vials 12 through the conveyor system 46. To these ends, the pumps 178 are preferably a venturi type pump as exemplified by a commercially available device known as a Model TT05 from Anver Corp. of Hudson, Me.

As shown best in FIG. 11, each pump 178 includes a power fluid inlet 180 having a solenoid operated valve 182 therein controlled by the computer 32 through a suitable communication link 184. The direction of the orifices inside the pump 178 act to apply a suction to the end of a pump inlet 186 connected to a stub conduit 188 that terminates immediately above the autoinjector tray 190 of the autoloader 18 of a conventional instrument 16. When a pressurized gas, such as air, is delivered through the power fluid inlet 180, a vial 12 in the tray 190 immediately below the end of the stub conduit 188 is lifted into the conduit 188 and delivered through the pump body 192 and pump discharge outlet 194 into the conveyor system 46 along with a sufficient quantity of air to propel any vial 12 to any desired location. This illustrates an important feature of this invention, which is the ability to retrieve vials 12 from the instruments 16 and deliver them through a conduit 104 to one or more receptacles 196, 198, 200. Normal vials 12, i.e. those having unknown materials therein which have been sampled and the tests appear to be normal as monitored by the computer 32, are conveniently delivered to a first receptacle 196 for temporary storage until the vials 12 are discarded. Abnormal vials 12, i.e. those having unknown materials therein which have been sampled but the tests appear to be abnormal or defective, are conveniently delivered to a second receptacle 198 so they may be readily retrieved for additional tests or retests. Vials 12 containing calibration samples are conveniently delivered to a third receptacle 200 so an operator can visually inspect the vials to determine if there is a sufficient quantity of material therein so the vial may be reused. In this event, the vial is replaced in the autoloader 108 for reuse. Those skilled in the art can readily determine additional categories of vials that might be desirable to collect after testing is complete and additional receptacles may be provided for that purpose. It will accordingly be seen that manual handling of the vials 12 is substantially eliminated except in the cases of a malfunction of the system 10 or some malfunctions of the instruments 16.

It will also be seen that the pumps 178 adjacent the autoloaders 44, 108 have the ability to pick up vials from the autoloaders 44, 108 and deliver them into the conveyor system 46 along with a sufficient volume of air to deliver the vials 12 to the instruments 16. Compressed air or other power fluid is delivered to the air inlet valves 182 of the various pumps 178 from a main compressor or high pressure air source (not shown) through suitable conduits (not shown).

In the event of an instrument malfunction, the vial 12 may be picked up by the pump 178 adjacent the instrument 16 that malfunctions and delivered through the conveyor system 46 to a receiver 202 which comprises a temporary holding location. As soon as a suitable instrument 16 is available, the vial 12 is picked up by the pump associated with the receiver 202 and delivered to the appropriate instrument 16.

It will be recognized that a considerable simplification has been achieved by transporting only one vial 12 at any one time. The software operating the computer 32 may potentially become sufficiently sophisticated to simultaneously transport two or more vials. The time to convey a particular vial 12 is rather short, usually measured in a few seconds for reasonable distances. There is accordingly plenty of time for the preparation station operator to load the autoloader 44 and for all other operations to be conducted in a timely, efficient manner.

Normally, the computer 32 is separate from the computer 30 running the software 30, so the computer 32 is in communication, through a link 204, with the computer 30 and thus is aware of the progress of tests being run on the instruments 16. The computer 32 accordingly comprises a monitor of the operation of the instruments 16. For example, gas chromatograph tests run on the instruments 16 have a predictable pattern. The GCs produce a series of peaks on a graph and detect a certain class of molecules first. The onset of the first peak, in a typical test, is received within a few moments of the onset of the test. If the computer 32 determines, from its communication with the computer 30 or from the converters 28, that the first peak has not been achieved within a reasonable time, the computer 32 can determine that some type malfunction has occurred at the GC in question and issues an alarm or instruction to the sample preparation station monitor 92 or to some other location where supervisory personnel can determine and solve the problem. For example, the failure to achieve a first peak within a predictable time period normally means that the autoinjector 18 has failed, often because of a broken or missing needle in the GC.

Other similar quality control techniques will be apparent to those skilled in the art where the computer 32 can monitor the computer 30 and conclude that something is amiss with a particular GC. For example, it may be known that a particular test should be conducted in a known time range. If the GC does not finish the test within the known time range, it is an indication that something is wrong with the GC. A suitable alarm or instruction can be displayed on the monitor 92 or other suitable device.

In the event the computer 32 detects that an instrument is not functioning and a vial has already been delivered to the autoinjector 18, the vial 12 can be retrieved and returned to the temporary storage receiver 202. The computer 32 can then instruct the conveyor system 46 to retrieve the vial 12 out of the holding receiver 202 and deliver it to an appropriate instrument 16 for testing.

An important feature of this invention is the degree of control and flexibility provided by the computer 32 and its associated software. In addition to the information in the data base 42, a second data base 206 may be provided containing the capabilities of the instruments 16. Thus, a particular sample in the data base 42 may be matched up with a particular instrument that is most suitable to run the necessary test on the sample. The computer 32 not only selects the sample to be run and controls its delivery to a particular instrument, the computer 32 also instructs the instrument 16, through the communication port 24 through the communication link 119 to run a test within the capability of the instrument 16. It will accordingly be seen that the computer 32 receives a variety of inputs from the instruments 16 in order to operate the system 10 including whether a particular instrument 16 is operational or has failed, whether a particular test is normal or abnormal, the capability of the instrument 16 or any other pertinent information about the instrument.

Figure 12:
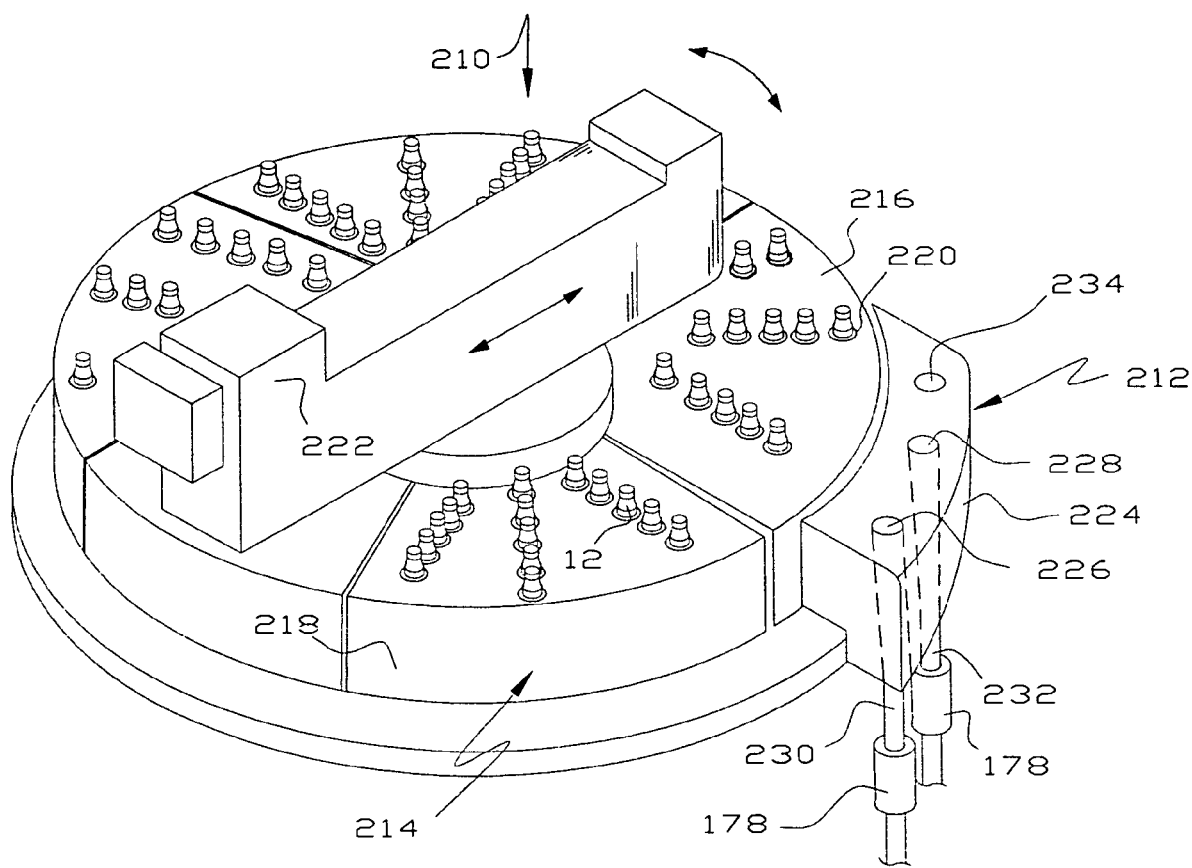
FIG. 12 is an isometric view of another embodiment of the autoloader of this invention.

Referring to FIG. 12, there is illustrated another embodiment of an autoloader 210 of this invention comprising a launcher 212 and a conventional autoloading tray 214 of any suitable type and which is illustrated as being part of an Agilent Technologies, Inc. gas chromatograph Model 6890, reference being made to publications of Agilent Technologies for more detailed information about the autoloading tray 214. The autoloading tray 214 comprises a circular platform 216, typically arranged in radial segments 218 providing recesses 220 for receiving sample vials 12. Conventionally, the platform 216 is stationary and the tray 214 provides a movable arm 222 capable of rotational and linear movement as controlled by one or more suitable stepper motors (not shown) to position the arm 222 at a location where vials 12 in the recesses 220 can be reached, picked up and moved to a desired location. The arm 222 in a conventional GC would deliver the vial 12 into the autoinjector. In this invention, the arm 222 delivers the vials 12 into the launcher 212.

The tray 214 is located at the sample preparation station 34 and is filled by an individual using a selector similar to the selector 82 shown in FIG. 6 to convert the autoloader 210 from a filling mode to a sending or transport mode. When the computer 32 sends a message to the monitor 92 that a vial 12 needs to be retrieved and sent, the worker moves the selector to the sending position. The arm 222 retrieves the vial 12 from the autoloading tray 214 and delivers it to the launcher 212.

The launcher 212 includes a housing 224 providing openings 226, 228 for receiving vials 12 and communicating with conduits 230, 232. After a vial 12 is placed in one of the openings 226, 228, the computer 32 delivers a signal to the pump 178 associated with the appropriate conduit 230, 232 to retrieve the vial and deliver it to the conveyor system 46 and then to an appropriate analytical instrument 16.

An RFID reader 234 may conveniently be housed in the launcher 212. As a matter of routine, the arm 220 may pass the vial 12 over the reader 234 to be certain that the vial 12 is the intended vial. It will accordingly be seen that the autoloader 12 operates in much the same manner as the autoloader 34.

Although this invention has been disclosed and described in its preferred forms with a certain degree of particularity, it is understood that the present disclosure of the preferred forms is only by way of example and that numerous changes in the combination and arrangement of parts, as well as the details of the components, may be resorted to without departing from the spirit and scope of the invention as hereinafter claimed.

I claim:

1. A system for transporting samples to and operating a bank of analytical instruments at least some of which include an automatic injector for delivering a liquid sample from a vial into the instrument, comprising
 a pneumatic conveyor using a gas as a propulsion fluid and including an inlet at a station, an outlet at selected ones of the automatic injectors and at least one conduit between the inlet and the outlets,
 an autoloader at the station including a removable tray having a large number of recesses for holding sample vials,
 a venturi having a low pressure inlet adjacent the tray for receiving a selected vial from one of the recesses, a power gas inlet and a high pressure outlet delivering the selected vial to the conveyor inlet for delivery to a selected one of the automatic injectors, and
 at least one computer communicating with at least some of the instruments and using information from the instrument as an input for controlling operation of the autoloader and conveyor.

2. The system of claim 1 further comprising a disposal receptacle and wherein the conveyor provides the capability of transporting vials from the autoloader to the instruments and of transporting vials from the instruments to the disposal receptacle.

3. The system of claim 1 wherein the instruments each comprise a communication port for communicating with an external device, the computer having a communication link for connection to the communication port.

4. The system of claim 1 wherein the system provides a series of elements for holding samples of unknown composition and a series of elements for holding samples of known composition and the controller periodically selects samples of known composition for delivery to the conveyor for calibrating at least one of the instruments.

5. The system of claim 4 wherein the autoloader provides the elements for holding the samples of unknown composition and further comprising a second autoloader for holding the samples of known composition.

6. The system of claim 1 wherein the station comprises a sample preparation station where liquids are taken from a container and placed in a vial and the vials are loaded into the tray.

7. The system of claim 1 wherein at least some of the instruments include a data output device and the computer includes a communication link with the data output device for monitoring operation of the instruments.

8. The system of claim 1 wherein the computer has the capability of conducting quality control operations on the instruments and delivering a signal in response to the quality control operations.

9. The system of claim 1 wherein at least one of the automatic injectors provides a recess to receive a vial from the conveyor and further comprising a venturi having a low pressure inlet adjacent the recess and a high pressure outlet in communication with one of the conduits whereby the venturi may suction a vial out of the automatic injector recess and deliver it into one of the conveyor conduits.

10. The system of claim 1 wherein the autoloader comprises an arm for retrieving the vial from one of the recesses and transferring it to the low pressure venturi inlet.

11. The system of claim 1 wherein the venturi is connected to one of the conveyor conduits so vials can pass from the conduit, into the outlet and then to the inlet.

12. A system for transporting samples to and operating a bank of analytical instruments at least some of which include an automatic injector for delivering a liquid sample from a vial into the instrument, comprising a pneumatic conveyor using a gas as a propulsion fluid and including an inlet at a station and an outlet at selected ones of the automatic injectors, an autoloader at the station for holding sample vials and presenting a selected one of the vials to the conveyor inlet for delivery to a selected one of the automatic injectors and at least one computer communicating with at least some of the instruments and using information from the instrument as an input for controlling operation of the autoloader and conveyor, the pneumatic conveyor comprising a plurality of distributors in series having at least one conduit connected at one end and at least a plurality of conduits at an opposite end, the conduits of a downstream distributor connecting each of the instruments to an upstream distributor so the computer can direct sample vials from the autoloader to each instrument.

13. The system of claim 12 wherein the conveyor comprises a receiver in the conduits adjacent the conveyor outlets, the receiver including means for slowing the vial at a location adjacent the instrument.

14. The system of claim 13 wherein the slowing means comprises a gate having a shoulder for abutting the vial.

15. The system of claim 12 wherein the conveyor comprises a receiver in the conduits adjacent the conveyor outlets and a sensor upstream of the receiver for detecting the passage of a vial and deenergizing the pneumatic conveyor.

16. The system of claim 12 wherein the outlet comprises a receiver for receiving a vial adjacent an end of the pneumatic conveyor, comprising
 a tubular housing having an axis in a direction of movement of the vial;
 a gate having an edge, the gate being biased for movement between a first position outside a path of movement of the vial toward a second position where the edge is inclined to the path of movement so an incoming vial contacts the edge and moves the gate toward the first position; and
 a motor for moving the gate from the second position to the first position.

17. The system of claim 12 wherein the autoloader comprises
 a base having an upstanding wall providing a series of horizontally and vertically spaced first openings for receiving the vials;
 a manifold inside the wall providing at least one second opening aligning with, and being in vial transferring relation to, different ones of the first openings in different positions of the manifold; and a motor causing relative movement between the base and the manifold between a plurality of positions for aligning the at least one second opening to a selected one of the first openings.

18. The system of claim 12 wherein the distributor comprises a housing having an inlet sleeve rotatably receiving an inlet conduit and a planar bottom wall having a plurality of outlets in a circular path for connection to a plurality of outlet conduits;

a rotatable article director in the housing having a rotatable disc providing a flat bottom abutting the planar bottom wall and providing an opening registering with the circular path, the inlet conduit being connected to the planar bottom wall around the opening for directing vials entering through the inlet opening to a selected one of the outlets in response to the rotational position of the disc;

a seal operative between the flat bottom of the rotatable disc and the planar bottom wall preventing leakage between the disc and the bottom wall; and a motor for rotating the rotatable article director in response to a command.

19. The system of claim 12 wherein the venturi is connected to one of the conveyor conduits so vials can pass from the conduit, into the outlet and then to the inlet.

20. The system of claim 12 wherein the distributor comprises a housing having an inlet connected to an inlet conduit of the pneumatic conveyor and a plurality of outlets connected to a plurality of outlet conduits of the pneumatic conveyor;

an article director in the housing having an opening registering with the housing inlet and an outlet movable between a plurality of positions aligned with the housing outlet; and a motor for moving the article director in response to a command between the plurality of positions.

21. The system of claim 12 wherein at least one of the automatic injectors provides a recess to receive a vial from the conveyor and further comprising a venturi having a low pressure inlet adjacent the recess and a high pressure outlet in communication with one of the conduits whereby the venturi may suction a vial out of the automatic injector recess and deliver it into one of the conveyor conduits.

* * * * *